US011839389B2

(12) United States Patent
Termanini

(10) Patent No.: US 11,839,389 B2
(45) Date of Patent: *Dec. 12, 2023

(54) ARTHROSCOPIC SHOULDER ARTHROPLASTY, COMPONENTS, INSTRUMENTS, AND METHOD THEREOF

(71) Applicant: JOINT INNOVATION TECHNOLOGY, LLC., Boca Raton, FL (US)

(72) Inventor: Zafer Termanini, Port Saint Lucie, FL (US)

(73) Assignee: JOINT INNOVATION TECHNOLOGY, LLC., Boca Raton, FL (US)

(*) Notice: Subject to any disclaimer, the term of this patent is extended or adjusted under 35 U.S.C. 154(b) by 0 days.

This patent is subject to a terminal disclaimer.

(21) Appl. No.: 16/330,321

(22) PCT Filed: Mar. 1, 2019

(86) PCT No.: PCT/US2019/020299
§ 371 (c)(1),
(2) Date: Mar. 4, 2019

(87) PCT Pub. No.: WO2019/173139
PCT Pub. Date: Sep. 12, 2019

(65) Prior Publication Data
US 2021/0386561 A1 Dec. 16, 2021

Related U.S. Application Data

(63) Continuation of application No. 15/911,128, filed on Mar. 4, 2018, now Pat. No. 10,595,886.

(51) Int. Cl.
*A61B 17/17* (2006.01)
*A61B 17/16* (2006.01)
(Continued)

(52) U.S. Cl.
CPC ........ *A61B 17/1778* (2016.11); *A61B 17/142* (2016.11); *A61B 17/144* (2016.11);
(Continued)

(58) Field of Classification Search
CPC .... A61F 2/4003; A61F 2/4014; A61F 2/4612; A61F 2/4607; A61F 2002/4044;
(Continued)

(56) References Cited

U.S. PATENT DOCUMENTS

| 597,915 A | 1/1898 | Roosa |
| 4,550,450 A | 11/1985 | Kinnett |

(Continued)

FOREIGN PATENT DOCUMENTS

| JP | H091224 A | 1/1997 |
| JP | 2002330983 A | 11/2002 |

(Continued)

OTHER PUBLICATIONS

International Search Report dated May 19, 2019, in connection with PCT International Application No. PCT/US2019/020299.

(Continued)

*Primary Examiner* — Brian A Dukert
(74) *Attorney, Agent, or Firm* — Norris McLaughlin PA

(57) ABSTRACT

A novel method and instrumentation for insertion of humeral and glenoid total shoulder implant using arthroscopic visualization for bony preparation as well as insertion of components through small incisions. Mini instruments and cannulated guides and reamers are used in order to perform the procedure under direct arthroscopic visualization. For ease of insertion, the components are inserted separately and assembled in situ. Securing the humeral components in place is accomplished with bicortical screw transfixing the central peg of component. Also disclosed are components, parts thereof and instruments used therewith.

16 Claims, 18 Drawing Sheets

(51) Int. Cl.
*A61F 2/40* (2006.01)
*A61B 17/14* (2006.01)
*A61B 17/15* (2006.01)
*A61F 2/30* (2006.01)
*A61F 2/46* (2006.01)
*A61B 17/56* (2006.01)

(52) U.S. Cl.
CPC .......... *A61B 17/15* (2013.01); *A61B 17/1633* (2013.01); *A61B 17/1659* (2013.01); *A61B 17/1684* (2013.01); *A61F 2/30749* (2013.01); *A61F 2/4003* (2013.01); *A61F 2/4014* (2013.01); *A61F 2/4081* (2013.01); *A61F 2/4612* (2013.01); *A61F 2/4637* (2013.01); *A61B 2017/564* (2013.01); *A61F 2002/305* (2013.01); *A61F 2002/30329* (2013.01); *A61F 2002/30476* (2013.01); *A61F 2002/30507* (2013.01); *A61F 2002/30574* (2013.01); *A61F 2002/4018* (2013.01); *A61F 2002/4635* (2013.01)

(58) Field of Classification Search
CPC ......... A61F 2002/4037; A61B 17/1778; A61B 17/1684; A61B 17/1664; A61B 17/1742
See application file for complete search history.

(56) References Cited

U.S. PATENT DOCUMENTS

| | | | |
|---|---|---|---|
| 4,893,619 A | 1/1990 | Dale | |
| 4,964,865 A | 10/1990 | Burkhead et al. | |
| 4,965,865 A | 10/1990 | Burkhead et al. | |
| 6,494,913 B1 | 12/2002 | Huebner | |
| 7,470,287 B2 | 12/2008 | Tornier et al. | |
| 8,753,402 B2 | 6/2014 | Winslow et al. | |
| 8,974,537 B2* | 3/2015 | Dreyfuss | A61F 2/4003 623/908 |
| 9,522,067 B2 | 12/2016 | Frankle | |
| 2003/0149485 A1 | 8/2003 | Tornier | |
| 2004/0143335 A1 | 7/2004 | Dews et al. | |
| 2005/0043805 A1 | 2/2005 | Chudik | |
| 2005/0107882 A1 | 5/2005 | Stone et al. | |
| 2009/0192621 A1* | 7/2009 | Winslow | A61F 2/4059 623/19.14 |
| 2011/0118846 A1 | 5/2011 | Katrana et al. | |
| 2014/0107652 A1 | 4/2014 | Walker | |
| 2014/0235540 A1 | 8/2014 | Gleicher et al. | |
| 2015/0223941 A1 | 8/2015 | Lang | |
| 2016/0235540 A1 | 8/2016 | Termanini | |
| 2022/0031464 A1* | 2/2022 | Knox | A61F 2/4014 |

FOREIGN PATENT DOCUMENTS

| | | |
|---|---|---|
| JP | 2005103286 A | 4/2005 |
| JP | 2008510526 A | 4/2008 |
| JP | 2014054543 A | 3/2014 |
| WO | 2006023980 A2 | 3/2006 |

OTHER PUBLICATIONS

International Search Report for corresponding application PCT/US2019/020299 dated May 22, 2019.
Translation of JP Office Action in corresponding application JP 2020-546120 dated Mar. 30, 2023.

* cited by examiner

US 11,839,389 B2

ARTHROSCOPIC SHOULDER ARTHROPLASTY, COMPONENTS, INSTRUMENTS, AND METHOD THEREOF

This is an application filed under 35 USC 371 based on PCT/US2019/020299, filed which in turn is based on U.S. Ser. No. 15/911,128 filed Mar. 4, 2018. The present application claims the full priority benefit of these prior applications and herein incorporates by reference the full disclosures of these prior applications.

FIELD OF THE INVENTION

The present invention relates to the use of patient specific shoulder implants and in particular to the use of instrumentation and guides for allowing the insertion of the components forming the shoulder prosthesis implant arthroscopically. The present invention also relates to a shoulder prosthesis and components thereof, tools and devices useful with the shoulder prosthesis, and methods for their use.

BACKGROUND OF THE INVENTION

Shoulder joint replacement has been practiced for many decades. The articular surfaces of the shoulder joint include a ball and a socket which may be damaged by trauma or degenerative disease. Pain and limitation of movement will require a replacement of the articular surfaces using a hemispherical humeral component and a shallow glenoid component. Damages to the rotator cuff and supporting structures will require the use of reverse shoulder implant, where the geometry of the components is reversed, and the humeral component is designed as a cupule while the hemispherical ball is attached to the glenoid plate.

However, the surgical procedure for the insertion of the prosthetic component requires significant surgical exposure that will unduly damage local anatomical structures such as surrounding muscles and adjacent tendons. Said damage will impose longer healing period and require extensive postoperative physical therapy. However, both anatomical shoulder implants as well as more recent reverse implants are traditionally inserted through conventional extensile surgical approach. Traditionally, the proximal humerus is reamed to allow for insertion of the stem of the humeral component. However, the existence of prior trauma and deformity of the proximal humerus preclude the use of implant with humeral stern. More recently, stem free or stemless humeral component are designed and used but remain bulky and require insertion through a conventional extensive surgical approach. The shoulder joint is anatomically a distraction joint as opposed to the hip knee and ankle joints which are weight bearing and compression joints. In the shoulder joint, compression forces are limited to lifting heavy objects when the arm is in the horizontal position. Conventionally used glenoid polyethylene components are known to flow and become loose leading to osteolysis.

BRIEF SUMMARY OF THE INVENTION

In one aspect, the present invention is directed to a novel method and surgical technique providing improved instrumentation for insertion of the components of a total shoulder prosthesis of my invention arthroscopically. thereby, minimizing damage to the surrounding muscles and supporting ligaments and tissues. In a further aspect, the present invention is directed to an implantable shoulder prosthesis, components thereof and parts thereof. In a still further aspect, the present invention is directed to instruments and devices useful with the arthroscopically implantable shoulder prosthesis, and methods for their use. Still other aspects of the present invention will become apparent from this patent specification and drawings.

An aspect of the present invention is to provide a surgical method for implantation of the parts of the humeral component and the parts of the glenoid components of my total shoulder prosthesis using arthroscopic techniques utilizing stab wounds and minimal surgical incisions. Minimal incisions are used to perform the initial steps of my method. The parts of the humeral component, as well as the parts of the glenoid components are assembled, in vivo, within the working space of the shoulder joint within the body of the patient to form the assembled humeral component and the glenoid component of my total shoulder prosthesis after each part has been inserted through the one or more stab wounds and minimal surgical incisions.

According to my method, an arthroscope is introduced superiorly and laterally via usual conventional techniques to visualize the anterior surface of the proximal humerus and the humeral head. Initially the humeral head is transected, which will debulk the joint and provide an accessible working space into the shoulder joint. An external osteotomy (cutting) guide (instrument) device having an arm and a cutting slot angled between about 30°-70° of inclination, preferably angled at about a 500 inclination with respect to the arm, is secured to the humerus preferably using a pin inserted percutaneously below the surgical neck of the humerus.

The osteotomy guide device is aligned along the anterior surface of the arm. A saw blade, preferably a mini-reciprocating saw blade advantageously having a plate blade guide part is then inserted anteriorly through a small anterior skin incision and passed through the cutting slot of the osteotomy guide and osteotomy of the head is carried out. Care is taken to avoid damage to the subscapularis tendon, attached to the interior surface of the humerus below the surgical neck. To facilitate the extraction of the head, it can be fragmented in the accessible work space and removed in pieces therefrom. A reciprocating saw blade, and/or a high-speed rotating burr may be used for this fragmentation under direct arthroscopic visualization. These tools are preferably configured for use through the cutting slot part of the osteotomy guide.

A next step is to prepare the humeral head to receive the implantable humeral component. A mechanical center locator is inserted through the first small anterior skin incision that will allow to locate the center of the humeral cut surface under direct visual supervision of the operating surgeon through the arthroscope. The humeral guide device comprises a mechanical center locator which is removably attached to one end of an outrigger, such allows the outrigger to be affixed to and separated from the mechanical center locator part when needed. A part of the outrigger is configured as a guide for the insertion of a guide pin through a stab wound of the lateral surface of the shoulder, to penetrate the lateral cortex of the humerus and allow the guide wire to exit through the cut surface of the humeral head, preferably at or near the center thereof. A cannulated shaft is then inserted (coaxially) onto the guide wire. A small circular boring reamer will be introduced over the guidewire, which will allow the small circular boring reamer to make a cylindrical central recess in the humeral cut surface which will accept a central peg part of a humeral component. The central peg has a suitably threaded central hole and an alignment recess which are used with a locator instrument, which is used to guide a drill and for boring a hole through the anterior surface of the proximal humerus for using a fixation screw for securing a part of the humeral implant.

The glenoid may be prepared for the provision of the glenoid component. In a preferred embodiment of my invention, the glenoid component is formed of metal or metallic materials, but may be of other materials. The glenoid component includes a base plate part which configured to be attached to a prepared glenoid surface. The glenoid component further includes an articular glenoid part which is adapted to be snapped in and secured in the recess of the attached glenoid base plate preferably via one or more locking tabs. Advantageously the articular glenoid part may have a convex surface which is preferably a polished metallic articular surface, or when the glenoid component is a reverse glenoid component, the articular glenoid part may have a concave surface which is also preferably a polished metallic articular surface.

Under direct vision, a central guide wire is inserted into the center of the glenoid fossa and a circular reamer is inserted onto the central guide wire and the reamer is used to shave the articular surface of the glenoid so to receive the base plate part of the glenoid component. Optionally but preferably a 3-hole template is introduced onto the guidewire that will facilitate the drilling of properly positioned holes for receiving the cancellous screws and the central peg, and thereafter, removed. Such a template includes holes corresponding to the placement of any central post and locations of any cancellous screws to be used in implanting the base plate part. The base plate part of the glenoid component is then introduced and secured in place to the glenoid with the cancellous screws having an appropriate length. The articular glenoid part will be subsequently snapped in and secured in the recess of the attached glenoid base plate via multiple locking tabs. In different embodiments, the articular glenoid part can be made from non-metallic materials, such as a synthetic polymer such as polyethylene, or may be ceramic. The contact surface with the bone may be cemented.

The metallic humeral component part is then introduced through the anterior incision and threaded over the tip of the compression rod. Alignment grooves at the end of the central peg will assure that the sliding sleeve and outrigger are properly aligned for the insertion of the fixation screw. Said fixation screw advantageously penetrates through the anterior and posterior cortices, providing better fixation than screw or other mechanical fixation means applied into weaker cancellous bone.

The polyethylene hemispherical head part of the humeral component is then squeezed in through the anterior skin incision and snapped onto the implanted metallic humeral component part. A hole for insertion of a fixation screw is then drilled, measured and taped. The fixation screw is then inserted in this place through the front incision.

The drawings and detailed description of the present invention are not intended to limit the invention to the particular form as disclosed, but the invention is to cover all modifications, equivalent and alternatives falling within the spirit and scope of the present invention.

BRIEF DESCRIPTION OF THE DRAWINGS

The present invention will be better understood upon reading the following detailed description of the drawings, without limitation of the general inventive concept, method of implantation, instruments and non-limiting embodiments thereof, and on examining the attached drawings, in which.

DETAILED DESCRIPTION OF THE INVENTION

Figure 1:
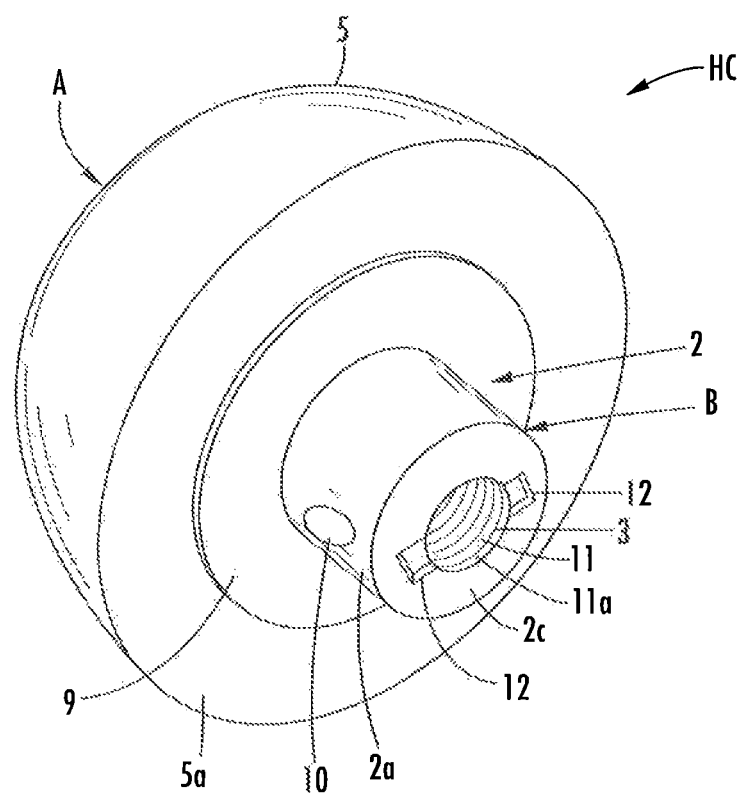
FIG. 1 shows a perspective view of a humeral component.

While the invention is susceptible to different changes and modifications, specific embodiments of the present invention are shown by way of example in the drawings and will be described herein in details. In the drawings, like reference numerals and/or letters refer to like elements in the various views.

Figure 7:
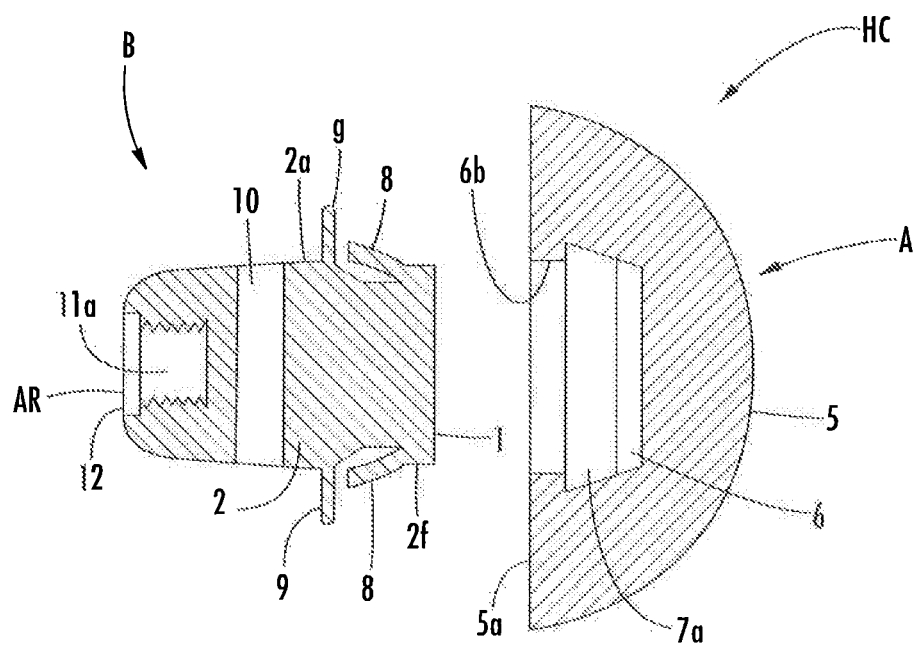
FIG. 7 shows a cross-sectional view of an implantable humeral component including the parts thereof.

Referring now to FIG. 1, and FIG. 7, thereon is depicted an embodiment of an arthroscopically implantable humeral component HC which comprises a head part A, affixable or affixed to a base part B. In the depicted embodiment the head part A includes a convex generally hemispherical articular surface 5, and the base part B, a fixation portion 2, which is desirably metallic. Said fixation portion 2 is generally cylindrical and comprises a central peg 2a at one end which is configured to be inserted into a part of a humerus, and the other end, comprises an insert portion 2b terminating at a generally flat end face 1 which is configured to be slidingly inserted into a recess 6 extending inwardly from the flat surface 5a of the head part A, which in the present embodiment is advantageously formed of polyethylene but may be formed of any other suitable material; such may be a metallic alloy or ceramic. The base part B includes an axial threaded recess 11 having threads 3 on the interior thereof, and as an alignment recess, AR, a transverse slots 12 recessed into the generally flat base 2c, the slots 12 spanning the open end 11a of the threaded recess 11. Further visible is a cylindrical hole 10 transverse to the central axis of the fixation portion 2 which passed into, but as shown preferably passes through a part of the central peg 2a, which hole 10 is sized to receive a fixation screw after the humeral component HC has been inserted and the fixation portion 2 compressed in place in the proximal humerus. It is to be noted here that the hole 10 does not necessary need entirely traverse the tapered central peg 2a but may terminate within the interior of the central peg 2a without necessarily passing completely therethrough as depicted in FIG. 7. It is also to be noted that in other embodiments, two or more holes 10 may be present in the base part B. Of particular importance is that the placement of any such hole 10 with respect to the alignment recess, AR, here transverse alignment slots 12 is to be observed, as the specific radial degrees of offset between the orientation of the alignment recess AR and the hole 10 may be used to determine the relative position of the hole 10 with regard to the alignment recess AR; such can be simply done by measuring from a reference point on the alignment recess (i.e., a corner or other part) and the distance from the base 2c of a hole 10 and the radial offset from the point on the alignment recess AR Such is discussed in more detail with reference to FIGS. 1A and 1B. This relative offset is used later in determining the location wherein a part of the humerus which is to be drilled and tapped after the base part B has been compressively inserted into the humerus, and more fully described with respect to later drawing figures. As a non-limiting example of FIG. 1 and FIG. 7 the radial offset between the position of the hole 10 and the position of the alignment slot 12 is 0° of arc, as a central axis of the hole 10 and a central lateral axis of the alignment slot 12 are in the same plane. It is to be understood that the radial offset may be any value other than 0° of arc, and where a plurality of holes 10 are provided, then a plurality of radial offsets may exist. It is only required that at least one radial offset or other relative position with the alignment recess AR (or part thereof) be determined and be known prior to implantation of the base part B within the humerus.

Figure 1A:
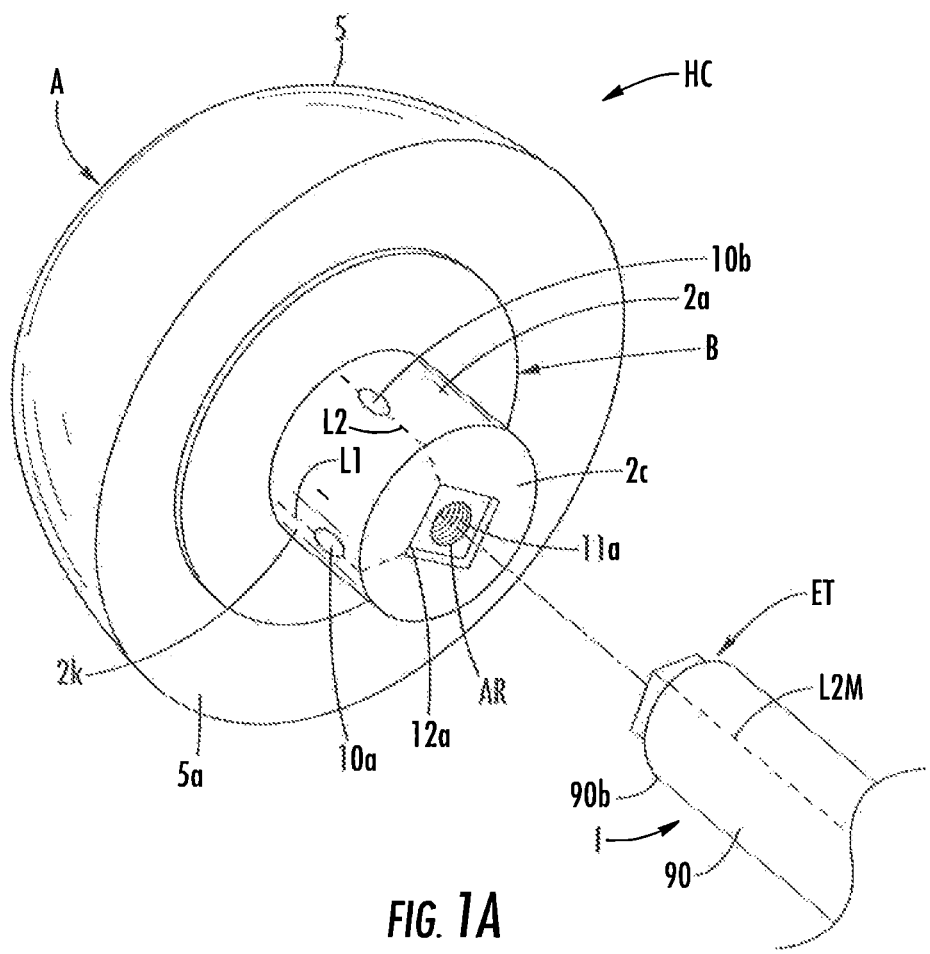
FIG. 1A shows a perspective view of a humeral component of a different configuration.

In alternative embodiments, instead of the alignment slots 12 as shown in FIG. 1 and FIG. 7, may be used other configurations of alignment recesses which engage with parts of other instruments. Such alternative alignment recesses may be other forms or geometries of recesses extending from the generally flat base 2c. Such for example may be any of essentially any configuration, and include without limitation: regular geometric shapes such as ellipses, triangles, squares, pentagons, hexagons, or may be simply the provision of one or more bores extending through the base 2c but spaced away from the open end 11a of the threaded recess 11, such as one or more bores into which a pin may be inserted. It is only required that such other forms or geometries of recesses be engageable with further instruments used in the method of the present invention, and be useful in referencing the position of the at least one hole 10 relative to the alignment recess AR. A non-limiting example of such an alternative embodiment of a humeral component HC is illustrated in FIG. 1A. As is seen there, the embodiment of FIG. 1A and FIG. 1 differs in that configuration of the alignment recess AR which is a generally square shaped alignment recess 12a having a relatively shallow depth terminating at a flat base 12c and having a center generally coincident with the center of the threaded recess 11. The embodiment of FIG. 1A also illustrates a central peg 2a having two offset holes 10a and 10b, here radially separated from one another by 90° of arc, and each entering through the sidewall 2k into the interior of the central peg 2a. As can be understood from the consideration of FIG. 1A, each of the two offset holes 10a and 10b is spaced at different distances from the base 2c. As can also be understood from FIG. 1A, each of the two offset holes 10a and 10b is coincident with different corners of the square shaped alignment recess 12a, i.e. hole 10a is coincident along (dotted) line L1, and hole 10b is coincident along (dotted) line L2. One or both of these corners may be used as a reference point of the alignment recess AR. In this way, the relative position of the holes 10a and 10b with regard to the alignment recess AR can be established. This spatial relationship can be in a manner transposed by using a further instrument (or part thereof) having an engaging tip ET which has a complementary geometry as that of the alignment recess AR. Thus, when engaging tip ET is appropriately inserted within the alignment recess AR, a corresponding mark L2M on an instrument I coinciding with a specific part of the alignment recess 12, here the corner thereof proximate to hole 10b whose placement is known to correspond to line L2, and as the position of hole 10b relative to both the alignment recess AR was known, and the length between hole 10b and base 2c was known, the position of a hole, i.e., hole 10b, of an implanted base part can be established using suitably configured further instruments (tools) appropriately engaging the alignment recess AR. In the embodiment of FIG. 1A, the holes 10a, 10b pass transversely through the base 2c.

Figure 1B:
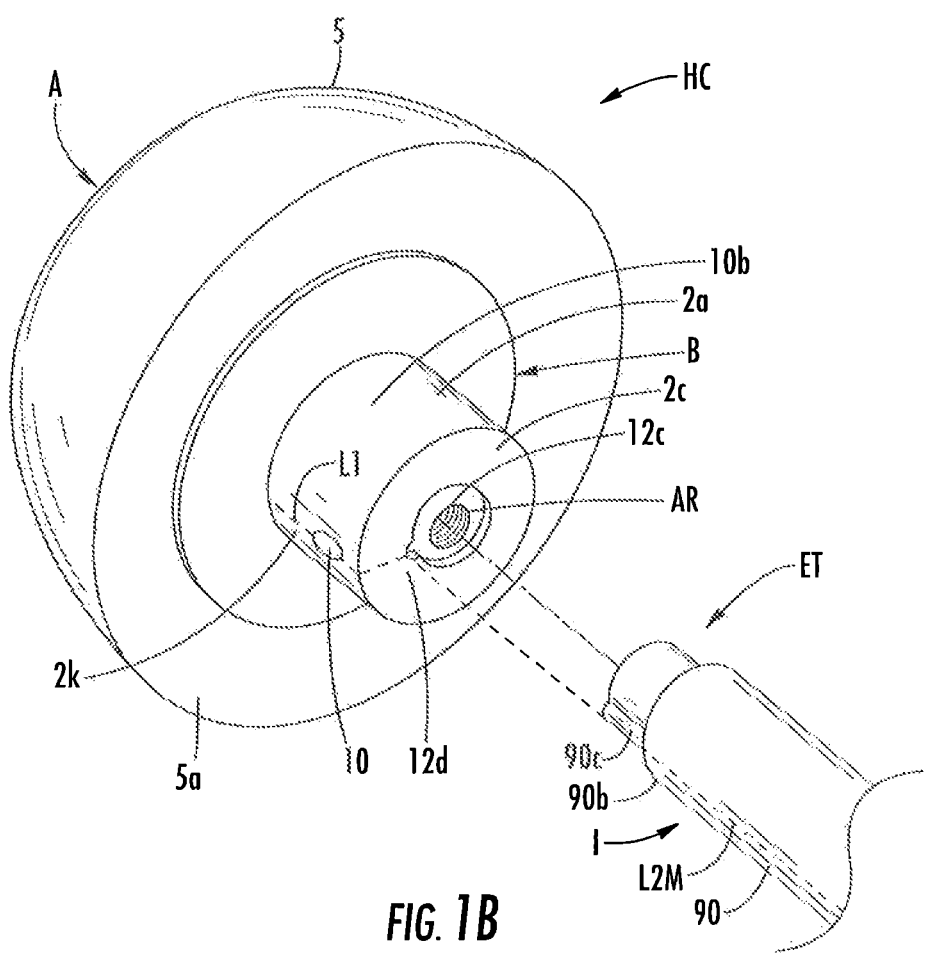
FIG. 1B shows a perspective view of a humeral component of a different configuration.
Figure 2:
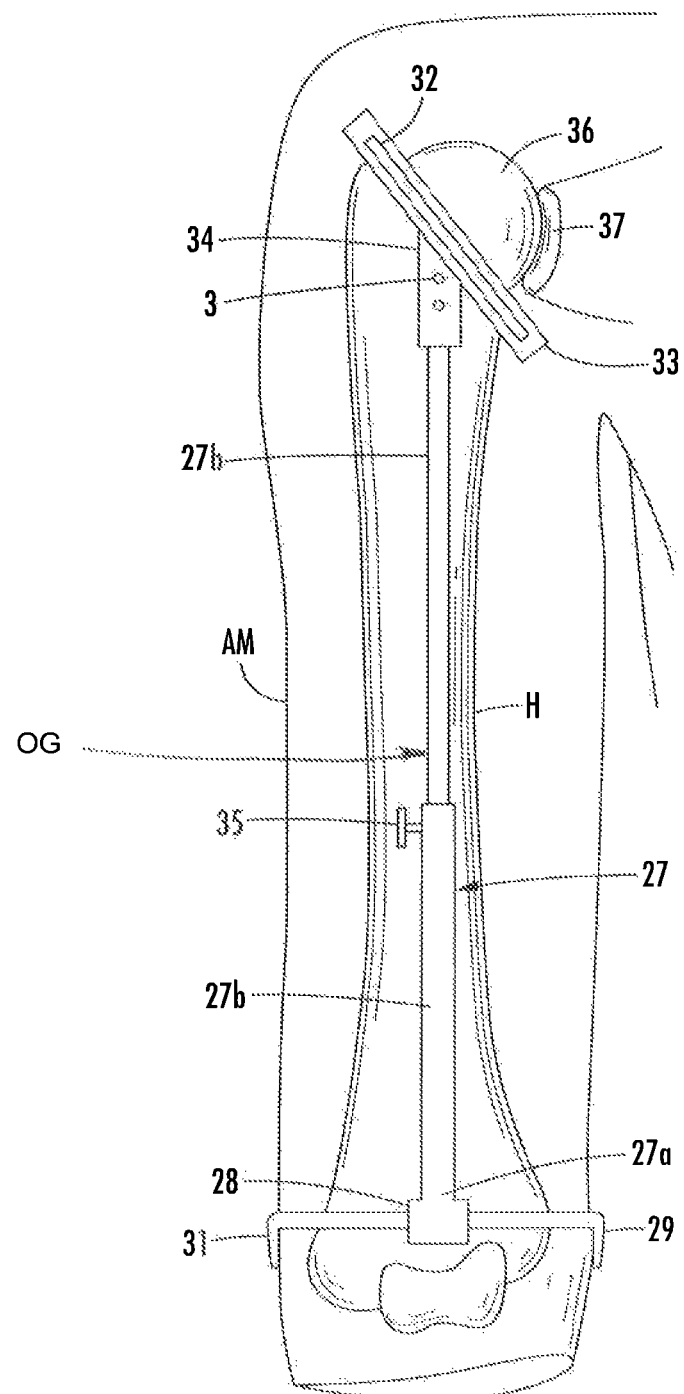
FIG. 2 shows a perspective view of the (external) osteotomy guide.
Figure 3:
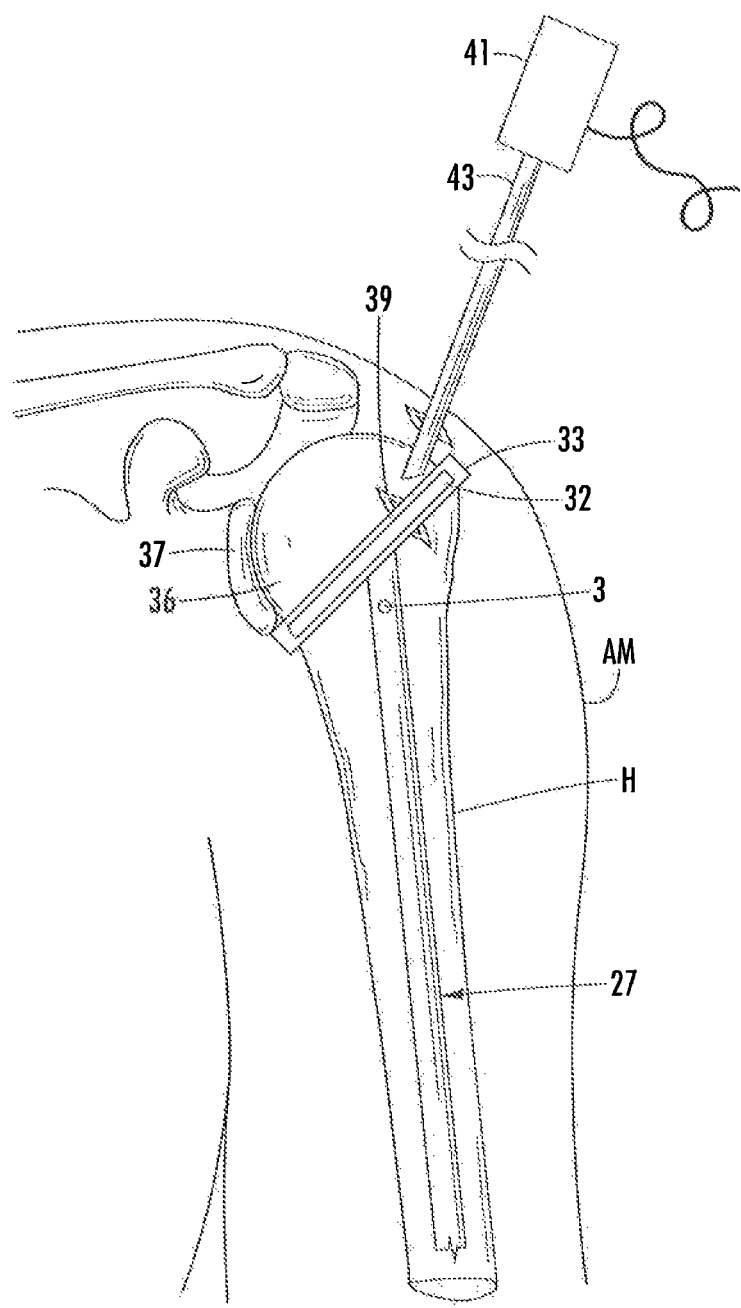
FIG. 3 shows a perspective view of a part of the osteotomy guide of FIG. 2 affixed with a pin to humerus under arthroscopic guidance.
Figure 4:
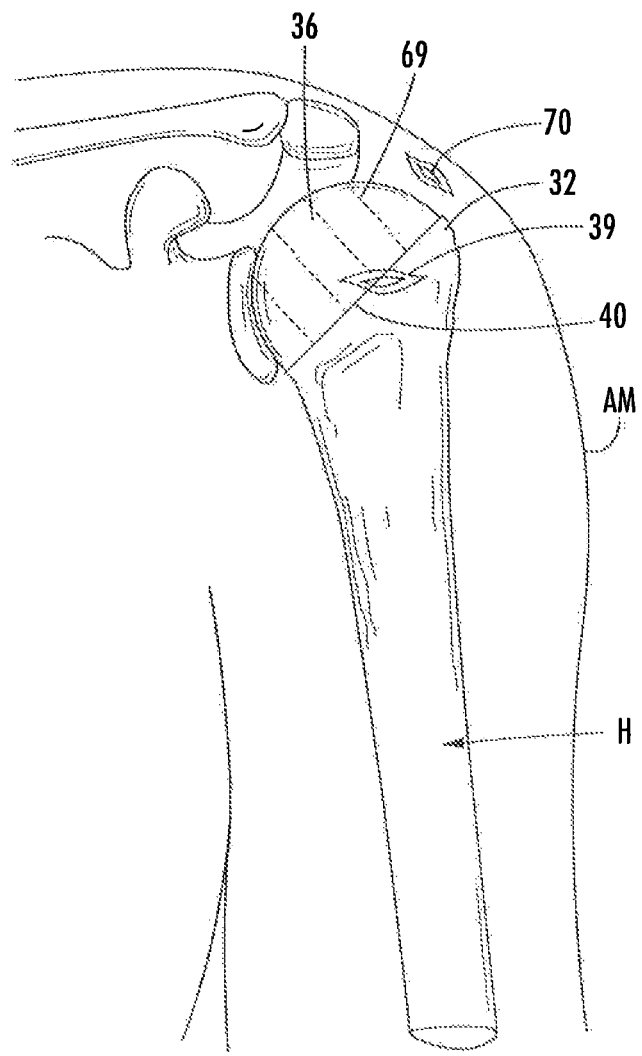
FIG. 4 shows a perspective view of the proximal humerus, entrance stab wounds and fragmental resection of the humeral head.

FIG. 1B illustrates a further non-limiting example of such an alternative embodiment of a humeral component HC similar in most respects to that illustrated in FIG. 1. As is seen there, the embodiment of FIG. 1B and FIG. 1 differs in that configuration of the alignment recess AR which is a generally circular 12a having a center generally coincident with the center of the threaded recess 11, and further having an inner sidewall recess 12d dimensioned to accept a spline 90c forming part of the engagement tip ET of a hollow locating sleeve 90. The alignment recess AR a relatively shallow depth terminating at a flat base 12c which comes into contact with locating sleeve 90. Thus, the engaging tip ET having the protruding spline 90C can only be inserted in one way (orientation) within the alignment recess AR, as the spline 90c can only be inserted within the inner sidewall recess 12d for the end of the engaging tip ET to be fully seated in the alignment recess and contacts the flat base 12c, thus fully engaging the alignment recess AR and the engaging tip ET. Thus, such a one way orientation is an embodiment of a "keyed" engaging tip ET which engages a suitably configured alignment recess AR, as the engaging tip ET can only be inserted into the alignment recess AR only one way. As all physical dimensions of the base part B is known and can be measured prior to its implantation, the distance of any hole 10 from the flat base 2c and its radial offset from the position of the inner sidewall recess 12d is known relative to the inserted engaging tip ET. In FIG. 1B, this relationship is shown by line L1 which shows that the center of the hole 10 is coincident with the midpoint of the inner sidewall recess 12 at the base 2c. Thus, correspondingly, any point on the locating sleeve 90 can be established with relation to the spline 90c forming part of the engagement tip ET, which can be used to establish the location of the hole 10 in relation to said point on the locating sleeve 90 when the alignment recess AR and the engaging tip ET are fully engaged with respect to each other.

The base part B comprises locking elements used to engage the base part B to the head part A. In FIG. 7 the locking elements are shown as (at least) two or more deformable or bendable locking tabs 8 which extend outwardly from the sidewall 2f of the insert part 2b and are configured to interlock into a circular groove 7 recessed (or which may be one or more other suitable recesses) in the inner sidewall 6b of the head part A; such provides a "snap fit" which securely attaches the base part B with the head part A, thus forming a complete, implantable humeral component HC. Other locking elements may also be used for the humeral component HC. The central peg 2a is optionally but preferably slightly inwardly (viz, towards its central axis) tapered, preferably at a taper angle of between about 0.5° to 10°, preferably at 2° to 5° of arc, for better retention in the humeral bone. As is best seen on FIG. 7, a circular disc 9, (alternately referred to as a flange 9) extends radially outwardly from the base part B and is situated between the insert part 2b and central peg 2a, which circular disc 9 is provided to reduce the flow of polyethylene under load and to stop further penetration of parts of the fixation portion 2 into the head part A, especially into the polyethylene thereof.

Figure 8:
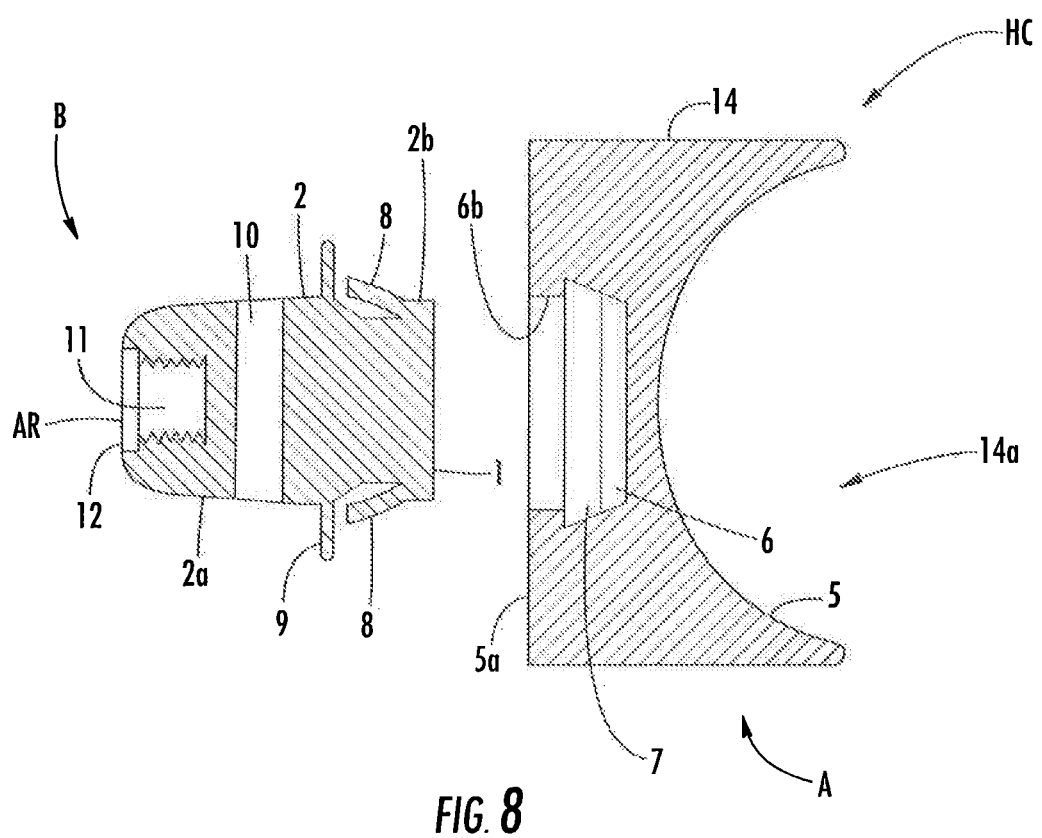
FIG. 8 shows another embodiment and cross-sectional view of an implantable reverse humeral component including the parts thereof.

In a further, albeit different embodiment than shown in FIG. 1 and FIG. 7, is that within FIG. 8, which embodiment is optionally referred to as a "reverse humeral component", having in its head part A, a geometry reversed to that as shown in FIGS. 1, 7. Here the head part A includes a concave generally hemispherical head 14, that is to say that it has a cavity or cupule 14a having a concave articular polyethylene surface 5, which is configured to come into interfacial contact with a convex hemispherical glenoid articular surface as may be seen on FIG. 11, which depicts a corresponding glenoidal component GC optionally referred to as a "reverse glenoid component" as it provides an interfacial contact surface with complements the concave hemispherical articular polyethylene surface 5 of the a cavity or cupule 14a of FIG. 8.

As mentioned earlier, an object of the present invention is to provide a method for insertion of and implantation of the humeral components and the glenoidal components of a total shoulder prosthesis using arthroscopic technique that will only require small stab wounds and significantly reduce skin incisions and surgical damage to the musculotendinous structures such as the subscapularis muscle.

Figure 5:
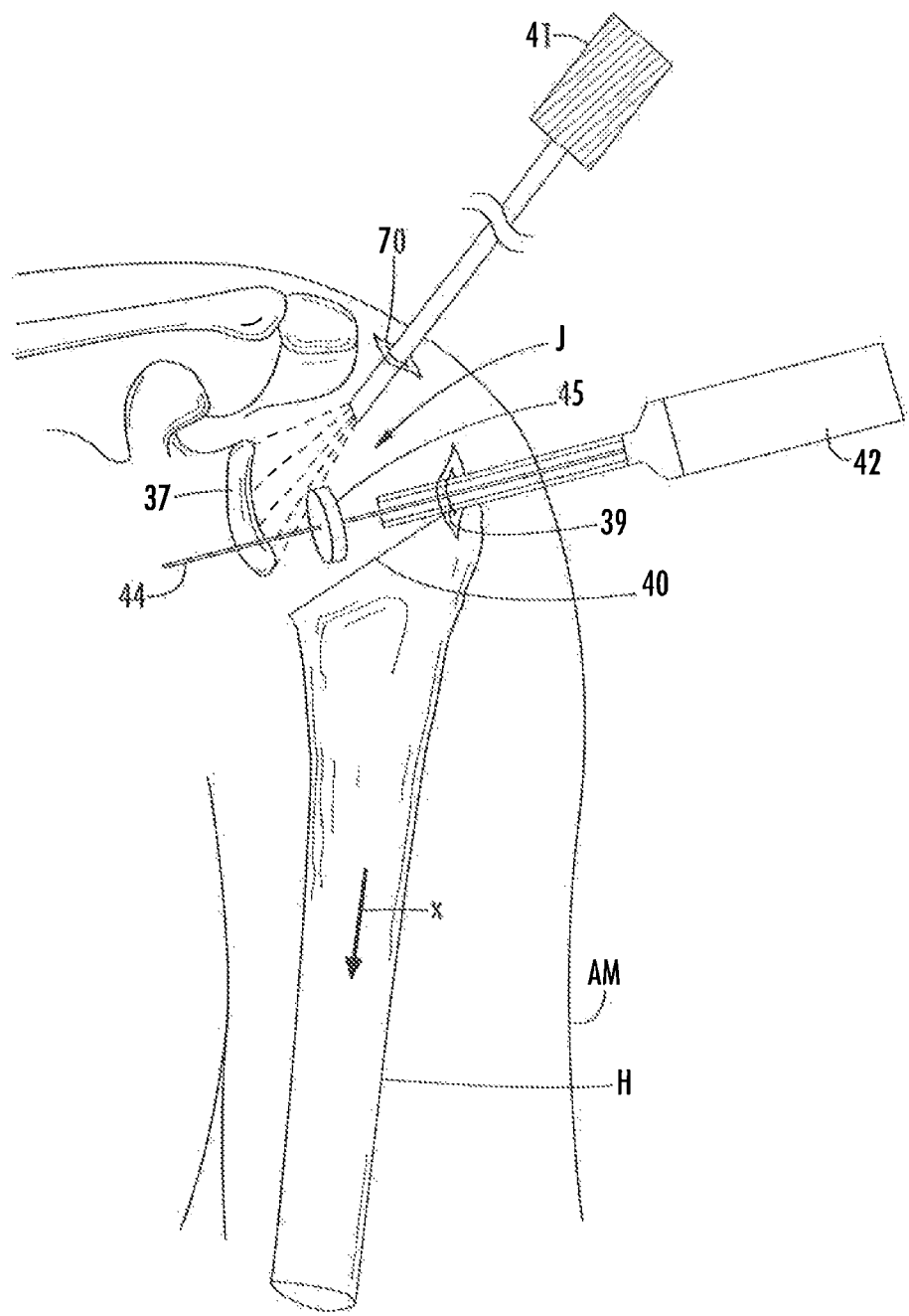
FIG. 5 shows the position of a powered circular reamer used in removal of glenoid fossa after the resection and removal of the humeral head.
Figure 6:
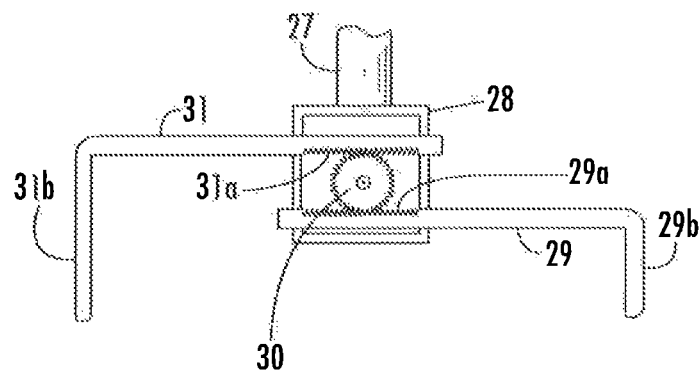
FIG. 6 shows the centering device at the distal end of the arm of the osteotomy guide of FIG. 2.
Figure 9:
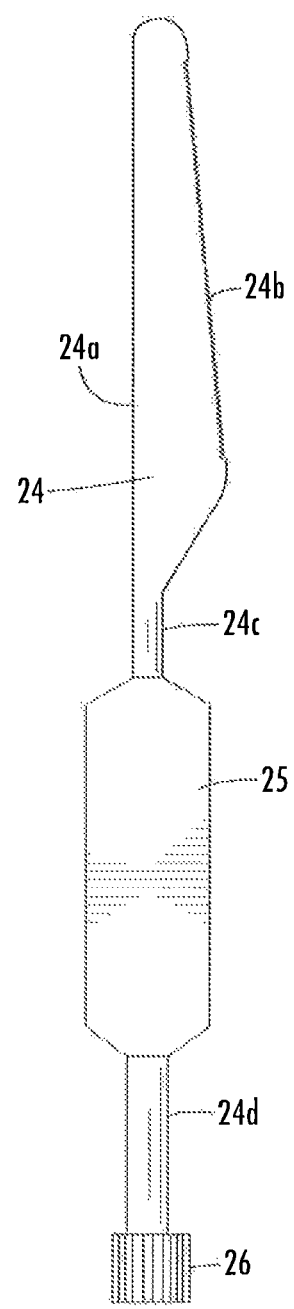
FIG. 9 shows a perspective top view of a mini reciprocating saw blade having a plate blade guide.

With reference now to FIGS. 2 to 6 and 9, in order to accomplish this object, according to the method, the humeral head 36 contacting the glenoid surface 37 is initially removed using an osteotomy guide 27 removably secured over the anterior surface of an arm. The osteotomy guide OG (also, osteotomy guide 27) is secured to the humerus H in a region of the humerus H proximal to the humeral head 36 using a pin 3, which pin is inserted through small stab wound in the skin of the arm AM and its position is visually controlled by the operating surgeon using arthroscopic camera 41 attached to arthroscope 43 introduced anteriorly and superiorly through a stab wound 70. A centering device 28 at the distal end of the arm 27b will assure that it is centered over the bony landmarks of the elbow including the medial 29 and lateral 31 epicondylar bony prominences. The distal end 27a of the osteotomy guide 27 is aligned over the anterior surface of the arm where medial and lateral expandable brackets 29 and 31 of the centering device 28 will assure that the osteotomy guide 27 is centrally located relative to the humerus H. As is best seen in FIG. 6, a part of each of the lateral expandable brackets 29 and 31 of the centering device 28 include a gear rack, respectively 29a and 31a which engage a center gear 30, whereby movement of either one of the lateral expandable brackets 29 and 31 is transferred to a similar movement via the center gear 30 to the other of the lateral expandable brackets 29 and 31. Distally from the gear racks 29a and 31a, each of the lateral expandable brackets 29 and 31 includes an angled end part, respectively 29b and 31b, configured to encompass a part of the arm AM therebetween. Optionally but advantageously the arm 27b is formed of two sliding or telescoping parts 27b which allows for the overall length of the arm 27b to be varied. Where two sliding or telescoping parts 27b comprise the arm 27b, a locking means such as a locking screw 35 (or other device or part(s)) may also be present to allow for the temporary fixation of the two sliding or telescoping parts 27b relative to each other. As can also be seen from FIG. 2, a proximal end of the arm 27b includes a bracket part 34 to which is affixed a cutting guide 33 having a lateral slot 32 angled between about 30°-70° of inclination, preferably angled at about a 500 inclination with respect to a center line of the arm 27b. As can be further seen from FIG. 2, at or near the distal end of the arm 27b is located the centering device 28. In preferred embodiments the centering device 28 may be repositioned on the arm 27b, and especially preferably can be rotated about the arm 27b so that it can be placed on the controlateral; such allows for the osteotomy guide 27 to be 'reversed' or 'flipped over' so that it may be used on the opposite shoulder joint of a patient. Returning to the method, a first mini incision 39 is made anteriorly and a mini-reciprocating saw blade as shown in FIG. 9 is introduced through slot 32 of the cutting guide into the joint. said saw blade 24 having a saw portion 24 having at one side saw teeth 24b, a blade shank 24c extending to a guide plate 25, the opposite end of which extends an attaching shank 24d which terminates in an attachment 26, adapted to be attached to a reciprocating conventional power driver. Guide plate 25 and the saw portion 24 are insertable within the slot 32 and the guide plate 25 will stabilize and ensure that saw blade 24 remains in the cutting plane defined by and parallel to the slot 32 at all time. The operating surgeon my encounter difficulty removing the humeral head because of deformity or size. Subsequently, guide 27 is removed and segmental extraction can be achieved by cutting the humeral head into several pieces or segments using the reciprocating saw which is introduced through first incision 39. The smaller resected fragments 69 can be withdrawn through the first incision 39.

Figure 15:
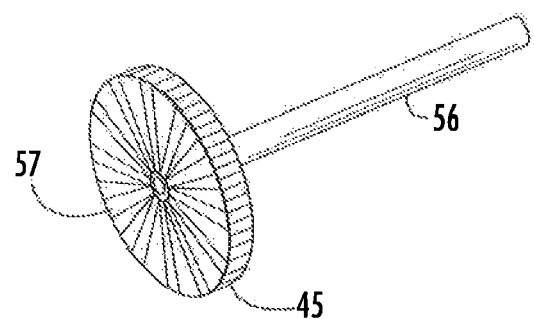
FIG. 15 shows in a perspective view the mini circular glenoid reamer.

A next step is to prepare the glenoid articular surface; see FIG. 5 and FIG. 15. In order to improve visualization of the glenoid cavity, the humerus H can be pulled downwardly (in the direction of arrow "x") and rotated externally in order to increase the working space J in the shoulder joint. A guide wire 44 is inserted in the glenoid surface 37 under direct arthroscope 41 visualization. A small circular reamer 45 attached to rotary power unit 42 which is then energized so that the reamer 45 is rotated and used to plane the surface FIG. 15, preferably to provide a generally flat surface to which the implantable glenoid component GC can be mounted (implanted). This operation may be repeated one or more times; the guide wire 44 may be inserted into a different part of the glenoid surface 37, and the surface prepared in this different additional surface part as described above, until a suitable surface satisfactory to receive a glenoid base plate part D. Once the glenoid surface is suitably prepared, a conventional drill guide (not shown) is inserted through first skin incision 39 and drill holes are made using long drill bits attached to an external rotary power tool 42.

Figure 10:
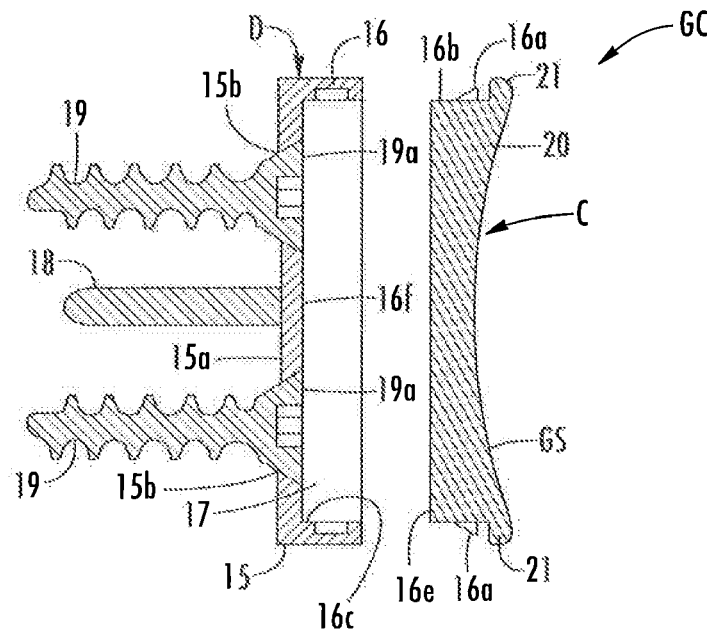
FIG. 10 shows a cross-sectional view of an implantable glenoid component including the parts thereof.
Figure 11:
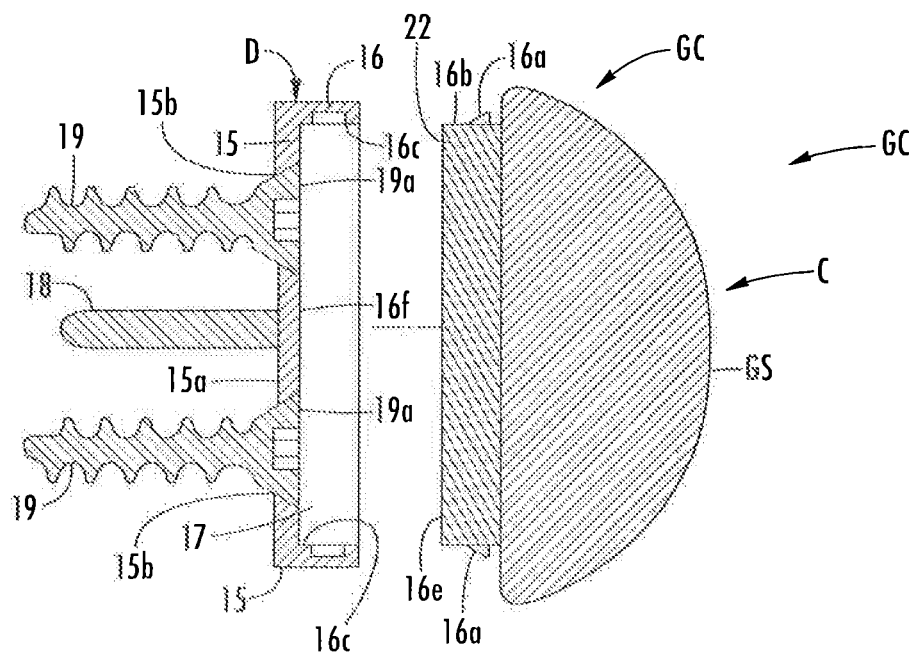
FIG. 11 shows a cross-sectional view of an implantable reverse glenoid component and the parts thereof.
Figure 12:
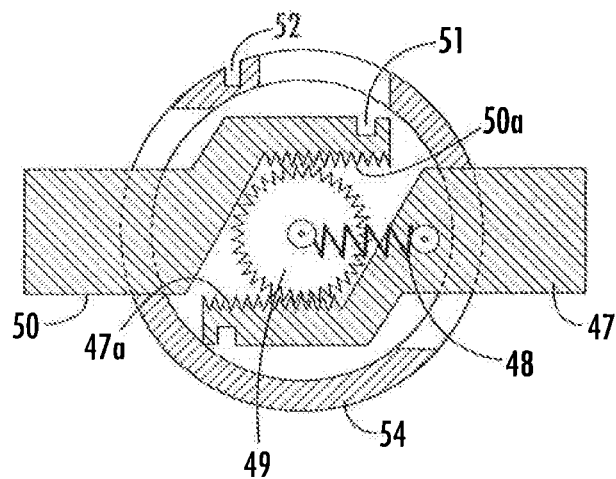
FIG. 12 shows top cross-sectional view of mechanical center locator part of a humeral guide device.
Figure 13:
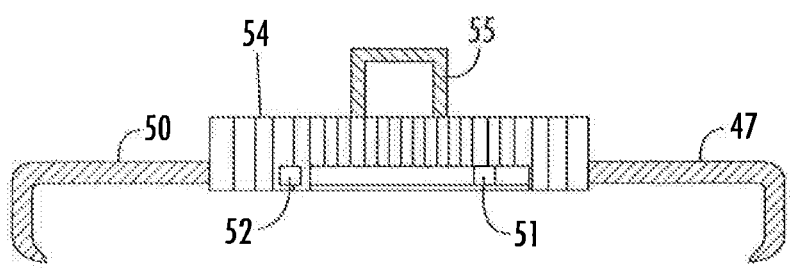
FIG. 13 shows a side view of the mechanical center locator part of FIG. 12.
Figure 14:
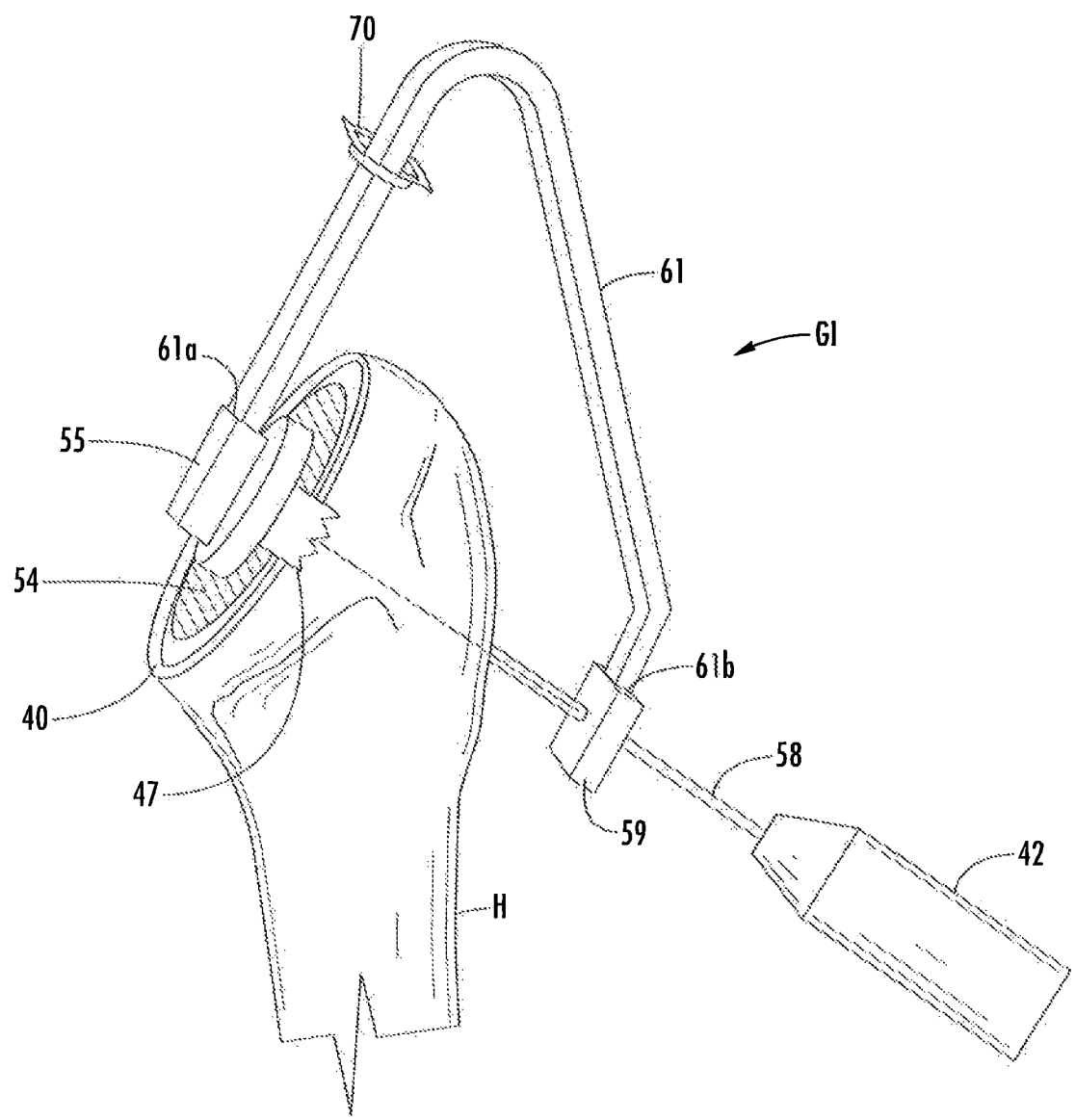
FIG. 14 shows a perspective view of the humeral center locator guide device attached to the detachable outrigger.

With reference now to FIGS. 10, 11, there are depicted two embodiments of an implantable glenoid component GC, each of which comprises an articular glenoid part C, affixable or affixed to a glenoid base plate part D. Returning now to the method, the glenoid base plate 15 is then inserted through incision 39 and secured to the prepared glenoid surface under direct arthroscopic vision using two (or one, or more than two) cancellous screws 19 after drilling and tapping. Optionally but preferably the base plate part D includes a central post 18 depending outwardly from lower face 15a the base plate 15 will stabilize it during screw insertion. The screws are inserted through suitably sized and placed screw holes 15b which are preferably chamfered to ensure that the heads 19a of the cancellous screws 19 are coincident with or below the generally flat base surface 16f within the cavity 17. The dimensions of the cavity 17 are such that a part of the articular glenoid part C, base 16e, can be received and retained therein. Also, while not illustrated in either of FIGS. 10, 11, the base plate part 15 is generally circular when viewed perpendicularly to the central post 18, which if present is advantageously coincident with a central axis of the base plate part 15.

Subsequently, the articular glenoid part C is inserted through skin incision 39 and snapped in securely in cavity 17 and secured by one or more locking tabs 16a extending out from a base sidewall 16b of the base plate part 15. The locking tabs 16a engage one or more suitably dimensioned locking recesses 16 in the inner sidewall 16c of the base plate part 15 when the base 16e of a corresponding articular glenoid part 20 or 23 is seated within the receiving cavity 17. It is to be understood that the embodiment of FIG. 10 illustrates a glenoid base plate part 15, and an articular glenoid part 20, having a concave (or a cupule shaped) articulating surface GS (or a cupule) which is adapted to come into interfacial contact with a humeral component HC having a head part A which includes a convex generally hemispherical articular surface 5 as shown in FIG. 1. Advantageously the articulating surface GS is a polished metallic articular surface, but may be a polymeric surface (i.e. polyethylene), a metal alloy or ceramic surface. FIG. 11 depicts a different embodiment of the present invention wherein the glenoid articular part 23 is of the "reverse" design and has a convex hemispherical geometry and a convex articulating surface GS; such is used with a hemispherical head part A of the humeral component HC (c.f FIG. 8) which is of a corresponding reverse geometry, that is to say that it has a cavity or cupule 14a having a concave articular surface 5. Advantageously the articulating surface GS is a polished metallic articular surface. Nonetheless, the arthroscopic insertion method remains the same for either a glenoid implant component of FIG. 10, or a reverse glenoid implant component of FIG. 11.

Figure 16:
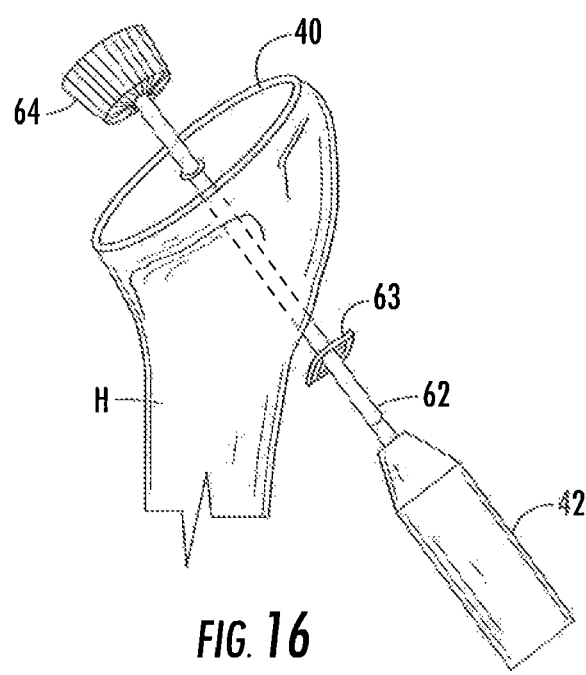
FIG. 16 shows in a perspective boring reamer used with the humeral implant.
Figure 17:
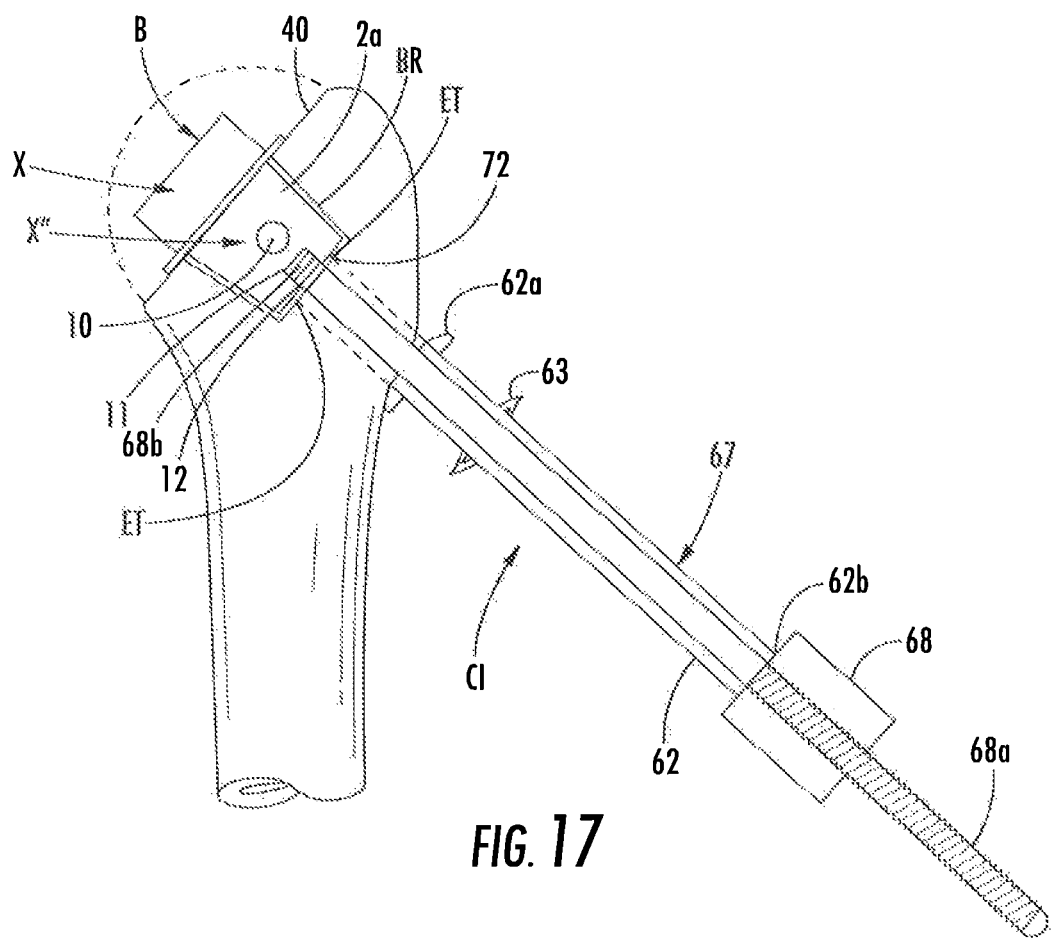
FIG. 17 shows sectional view of a compression instrument.

The next step is preparing the humeral cut surface for insertion of the humeral component. With reference to FIGS. 12, 13, 14, 16, 17, 18, mechanical center locating part 54 of a guide instrument (GI) is introduced through the anterior incision 39 and placed onto the cut, flat surface 40 of the humerus H. The position of the device is checked directly by the surgeon through the arthroscope inserted superiorly through stab wound 70. The claws 47 and 50 are squeezed open using a surgical clamp (not shown) where the two small recesses 51 and 52 are squeezed. As can be seen from FIG. 12, a part of each of the claws 47 and 50 include a gear rack part, respectively 47a and 50a which engage a center gear 49, whereby movement of either one of the claws 47 or 50 is transferred to a similar movement via the center gear 49 to the other of the claws 47 or 50. Once the surgical clamp is released the claws 47 and 50 will be closed by the spring 48 which urges the claws 47 50 in the direction of the center gear 49, thereby holding the mechanical center locating part 54 securely on the cut surface 40 of the humerus H. As the length of the claws 47 and 50 are preferably the same, the mechanical center locating part 54 provides a self-centering function relative to the cut, flat surface 40 of the humerus H. The outrigger 61 is then attached via its proximal end to the mechanical center locating part 54 through the upper incision 70 and inserted into attachment channel 55. As is seen preferably the cross section of the attachment channel 55 is non-circular, here it is square, as a non-circular cross section aids in secure affixation of an outrigger 61 and limiting its rotation relative to the mechanical center locating part 54. The outrigger 61 will facilitate the accurate insertion of the central guide wire 58 via a perforated guide 59 at the opposite, distal end 61b of the outrigger 61 which will also be used to insert the tapered humeral bore reamer 64 and will also facilitate to accurately drill a recess in a part of the humerus so to correspond to a hole 10 (c,f. FIG. 17) and to tap the proximal humerus H for insertion of the fixation screw 75. A cannulated shaft 62 (or other hollow shaft 62) is inserted over the guidewire (c.f. FIG. 16) and brought out in the center part of the humeral cut surface 40. Said cannulated shaft 62 is threaded at its proximal tip; a circular boring reamer 64 having a centrally threaded portion will be introduced through main incision 39 and threaded onto the threaded tip of cannulated shaft 62 (c.f. FIG. 16). The distal end of the cannulated shaft 62 is operably attached to a rotary power unit 42, which causes the humeral bone reamer (which is preferably tapered inwardly) to rotate and cutting into the central portion of the humeral cut surface 40 is arthroscopically observed until a suitably sized central recess BR is bored into the humerus H for receiving peg 2a of the base part B. Subsequently, the base part B is introduced through first incision 39 where the central peg 2a is inserted in the bored central recess BR.

To accomplish compression of the base part 2 into the bored central recess BR, a compression instrument 67 (CI) is utilized (c.f. FIG. 17). The compression instrument CI has a slideable shaft 68a having threads at opposite ends thereof at least partially within a cannulated (or hollow) sleeve body 62. The sleeve body 62 has a shoulder 62a at a proximal end thereof, and a distal end thereof 62b. The proximal end of the compression instrument 67 is introduced through lateral stab wound 63 and to buttress the shoulder 62a adjacent to a passage P through the humerus and the shaft 68a extended through passage P until a set of threads 68b at the proximal end of the shaft 68a is threaded into the threaded recess 11 of the central peg 2a. With the shoulder 62a in abutment with the lateral cortex of the humerus, rotation of knob 68 moves shaft 68a distally, (i.e., away from the joint) and draws in and compresses the central peg 2a into the bored recess BR of the humerus H. The base part B is thus seated into the bored recess BR under compression provided via the rod 68b. The central peg 2a is seated until the circular disc 9 is coincident with, or rests upon the cut flat surface 40 of the humerus H. The compression instrument 67 may be withdrawn, (or alternately only the sleeve body 62 and knob 68 removed, as in certain embodiments the rod 68a may be used to form part of the locating instrument (LI).

Figure 18:
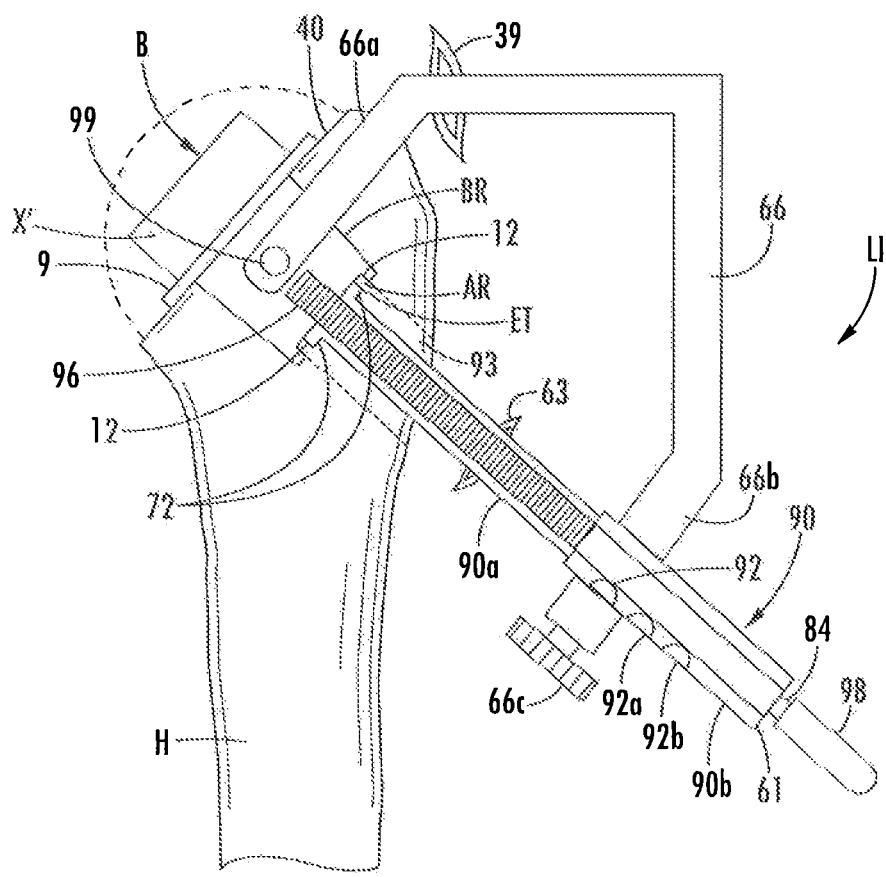
FIG. 18 is perspective view of a locator instrument.
Figure 19:
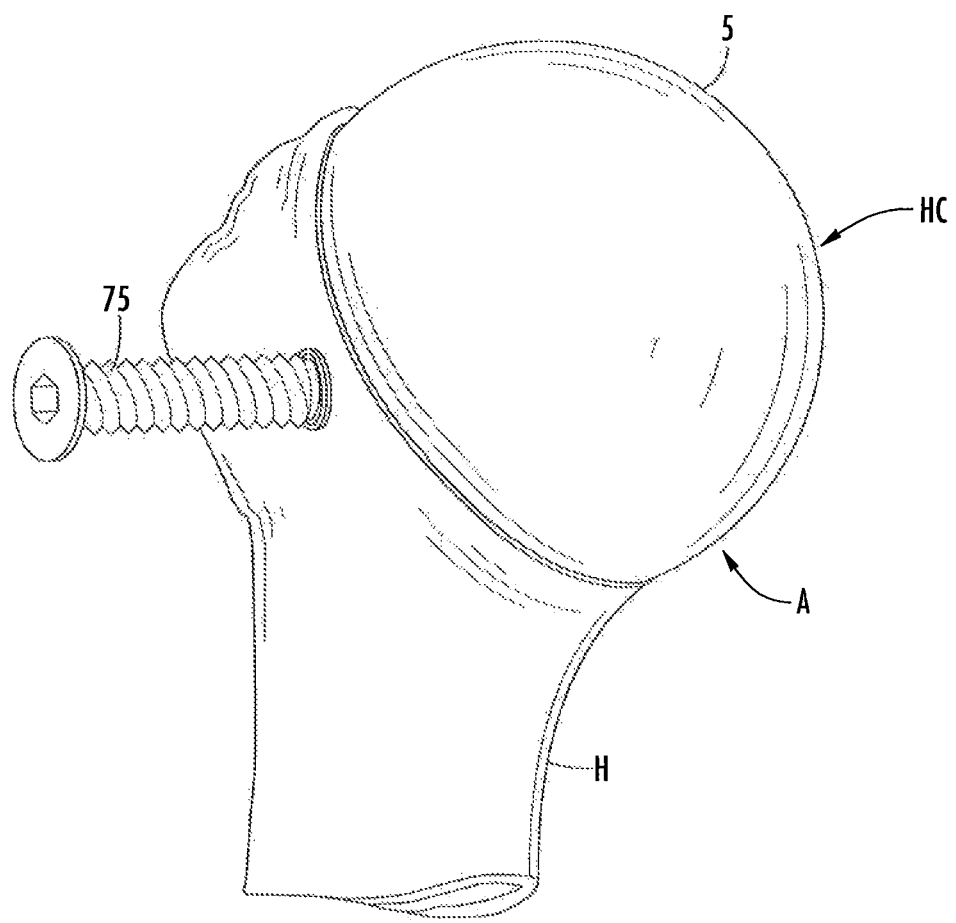
FIG. 19 is a perspective view of an implanted humeral component and a fixation screw partially inserted into proximal humerus.

The subsequent insertion of the locking fixation screw 75 (c.f FIG. 19) requires accurate drilling and tapping of the proximal humerus so that the screw 75 is engaged within a hole 10 of an implanted central peg 2a. To achieve this end, a locating instrument LI comprising at least a hollow locating sleeve 90 having a proximal part 90a having at its proximal end thereof 90b an engaging tip ET, here a pair of alignment tabs 72 which have a complementary geometry as that of the alignment recess AR of the base part B, here the alignment slots 12 within the central peg 2a. The diameter of the passage P through the humerus H is sufficient to allow insertion of the proximal end 90b and the outwardly extending alignment tabs 72 therein, thereby mechanically engaging and positioning the locating sleeve 90 relative to the implanted central peg 2a and all elements of the base part B, notably any holes 10. (Here, and with reference to FIG. 1A, where the configuration of the engaging tip ET is different than shown in FIG. 18, a passage P of a smaller diameter or dimension may be sufficient to permit for insertion of such engaging tip ET with an alignment recess AR having a suitable complementary geometry, and allow for proper location of a hole 10, in a manner similar to that described here.) The hollow locating sleeve 90 further comprises a distal part thereof 90b preferably conjoined with the having a proximal part 90a. While the proximal part 90a is advantageously has a hollow circular cross-section, the distal part 90b advantageously has a hollow non-circular cross-section, i.e., is square, pentagonal or hexagonal cross section although a circular cross-section may also be used but may be less suitable. It is to be understood from the foregoing and from the drawing of FIG. 18 that the two parts of the hollow locating sleeve 90 have a length dimension which can be determined to any place or point on the hollow locating sleeve 90 from the engaging tip ET, such that when the engaging tip ET (here the alignment tabs 72) is engaged in the alignment recess AR (here the alignment slots 12), correspondingly any point, or hole 10 in an implanted central peg 2a can be established as a distance from any place or point on the hollow locating sleeve 90. This spatial relationship is used to locate one or more such holes 10 utilizing a further part of the locating instrument LI, a locator outrigger 66. When the engaging tip ET is seated within the alignment recess AR, which may be facilitated by an indexed mounting rod 98 having a threaded proximal end 96 engaging the axial threaded recess 11, and at or near a distal end thereof one or more index marks 84, the locator outrigger 66 may be removably affixed to a part of the distal part 90b. As the locator outrigger 66 is preferably rigid, its length from a locator hole 99 in a proximal arm end 66a thereof from a distal clamp arm end 66b is constant, such that the position of the locator hole 99 can be overlaid over the position of a hole 10 in an implanted central peg 2a by suitably locating the locator outrigger 66 with respect to the locating sleeve 90. The position of the locator outrigger 66 may be established by affixed it at a position on the locating sleeve 90 by any suitable means, and its position may be varied. The embodiment shown in FIG. 18 depicts a preferred embodiment wherein the configuration of the distal clamp arm end 66b has a cross-section complementary to that of the shape of the cross-section of the distal part 90b, thus making a non-circular cross-section, i.e., a triangular, square, pentagonal or hexagonal cross-section advantageous as such which provide good rotational stability of the locator outrigger 66 and the engaged locator sleeve 90, which is preferably positioned so that its end 61 is coincident with an index 84, which assures that the engaging tip ET is seated within the alignment recess AR. The locator outrigger 66 is then mountable relative to (or indexed relative to) one or more hole reference positions, such as by using a knurled screw 66c the end of which may be pointed to be received by a positioning recess 92 (and/or 92a, 92b) which are located on the distal part 92b of the locator sleeve 90 at positions (i.e., 92, 92a, 92b) which are known to provide proper placement of the locator hole 99 over a hole 10 of an implanted central peg 2a. Such a positioning recess 92 represents a non-limiting example of an "hole reference positions" position which may different in different embodiments, i.e., may be a line or mark present on a part of the locating sleeve 90 which is used to align these two parts. Thereafter a conventional surgical drill can be inserted through the locator hole 99 and used to bore a hole through the humerus H will be coincident with a hole 10. To avoid damage to soft tissue, after the locator outrigger 66 is in place over the hole, a further small incision is made and a hollow guide sleeve (not shown) is inserted through this further small incision to isolate surrounding soft tissue and to allow the guide sleeve to be inserted into the locator hole 99 or abutting the locator hole 99. A suitably sized drill and/or tap is then inserted through this guide sleeve and used to drill and/or tap the humerus H; thereby cutting edges of the drill and/or tap are isolated from the surrounding soft tissue. Subsequently the locator instrument LI or parts thereof such as the locator outrigger 66 may be removed, prior to or subsequent to tapping of the bored hole and insertion of a fixation screw 75 which will engage at least a part of a hole 10. The fixation screw 75 inserted and screwed in through the cortices of the humerus H, thus immobilizing the central peg 2a relative to the humerus H. The head part A of the humeral component HC, is then squeezed into the shoulder joint through the main incision 39 and snapped onto and locked onto the base part B of the humeral component, B, which component is preferably metallic. 2. See FIG. 19. Upon completion of the component insertion, the passage P made over the lateral surface of the humerus are plugged with bone graft. Any remaining instruments or parts may then be removed and all wounds sutured or otherwise sealed as appropriate.

It is to be understood that each of the parts of the humeral component and the parts of the glenoid components may be of different sizes and dimensions, and that during implantation it may be beneficial to have a plurality of each of the components of different sizes available so that test fitting may be undertaken during the implantation surgery. Thus, kits comprising two or more parts used to form a humeral component or glenoid component, the parts having different sizes or dimensions may be provided and are also contemplated as being aspects of the present invention.

Figure 20:
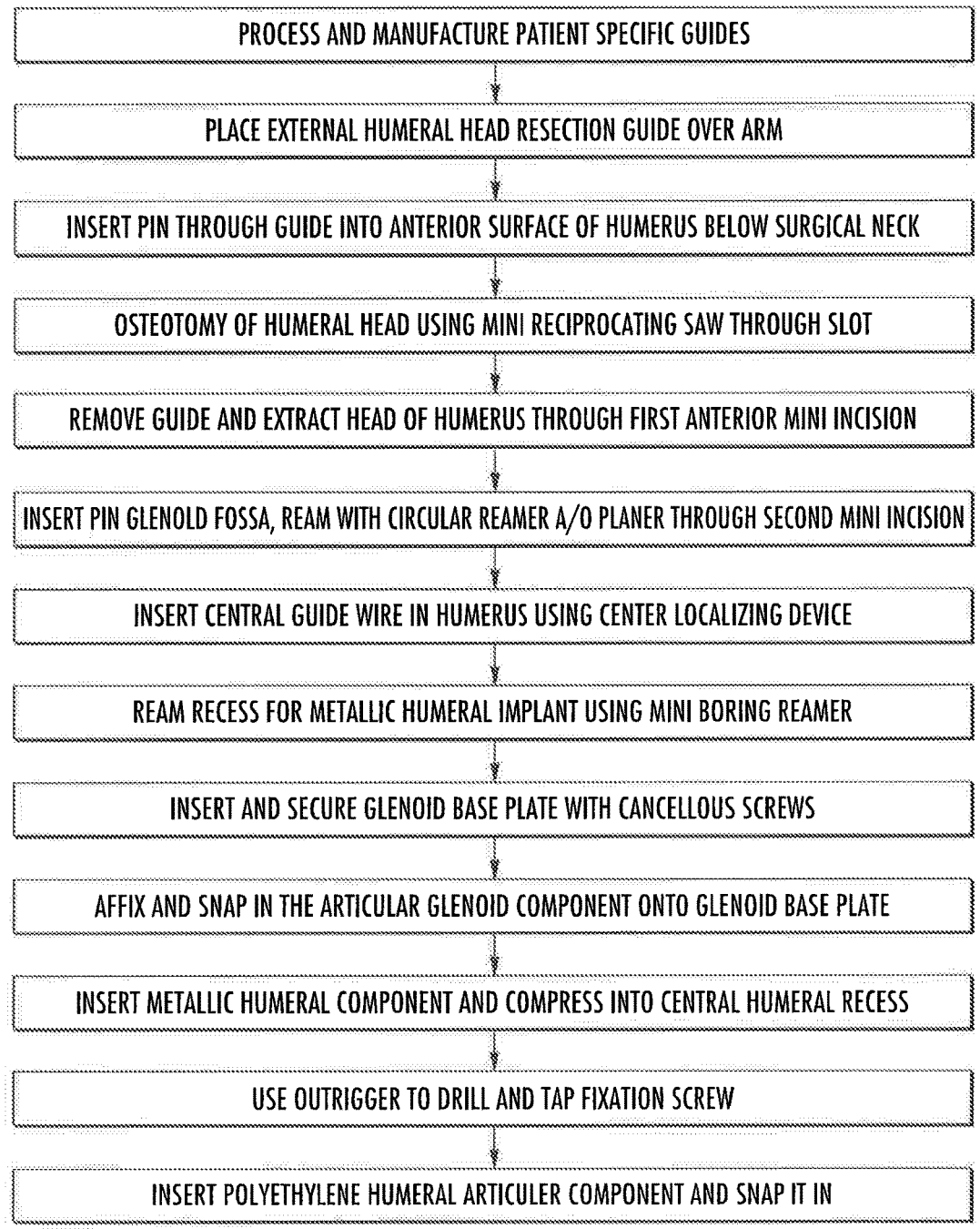
FIG. 20 is a flowchart of a method of the present invention.

FIG. 20 is a flowchart of method steps according to one aspect of the present invention.

In a further aspect of the invention, there is provided a kit of component parts which may be assemble a suitably dimensioned implantable humeral component HC, which kit comprises at least one, but preferably a plurality of individual head components A which may be of the same dimensions but which preferably have differing dimensions or configurations of at least the hemispherical head part A and optionally but preferably also, at least one base part B adapted to be affixed to one or more of the hemispherical head parts A comprised in the kit. The kit may be supplied within one or more sterilized or serializable seals, trays or containers which contain the foregoing parts.

In a still further aspect of the invention, there is provided a kit of component parts which may be assemble a suitably dimensioned implantable glenoidal component GC, which kit comprises at least one, but preferably a plurality of individual articular glenoid parts C which may be of the same dimensions but which preferably have differing dimensions or configurations of at least the articular glenoid parts C and optionally but preferably also, at least one glenoid base plate part D adapted to be affixed to one or more of the articular glenoid parts C comprised in the kit.

The kit may be supplied within one or more sterilized or serializable seals, trays or containers which contain the foregoing parts.

In a further aspect of the invention there is provided a kit which comprises:
(a) component parts which may be assembled into a suitably dimensioned implantable humeral component HC, which kit comprises at least one, but preferably a plurality of individual head components A which may be of the same dimensions but which preferably have differing dimensions or configurations of at least the hemispherical head part A and optionally but preferably also, at least one base part B adapted to be affixed to one or more of the hemispherical head parts A comprised in the kit; and,
(b) component parts which may be assembled into a suitably dimensioned implantable glenoidal component GC, which kit comprises at least one, but preferably a plurality of individual articular glenoid parts C which may be of the same dimensions but which preferably have differing dimensions or configurations of at least the articular glenoid parts C and optionally but preferably also, at least one glenoid base plate part D adapted to be affixed to one or more of the articular glenoid parts C comprised in the kit. The kit may be supplied within one or more sterilized or serializable seals, trays or containers which contain the foregoing parts.

In a still further embodiment there is provided a kit contain a compression instrument CI, and/or parts of a guide instrument GI. The kit may be supplied within one or more sterilized or serializable seals, trays or containers which contain the foregoing.

In a still further embodiment there is provided a kit contain a compression instrument CI, and/or parts of a compression instrument CI. The kit may be supplied within one or more sterilized or serializable seals, trays or containers which contain the foregoing.

In a still further embodiment there is provided a kit contain a locator instrument LI, and/or parts of a locator instrument LI. The kit may be supplied within one or more sterilized or serializable seals, trays or containers which contain the foregoing.

In a still further embodiment there is provided a kit, which comprises a one or more parts which may be assemble a suitably dimensioned implantable humeral component HC and/or one or more component parts which may be used to assemble a suitably dimensioned implantable glenoidal component GC. Optionally the kit may be provided with a compression instrument CI, and/or parts of a compression instrument CI. Optionally the kit may be provided with a locator instrument LI, and/or parts of a locator instrument LI. The kit may be supplied within one or more sterilized or serializable seals, trays or containers which contain the foregoing.

A yet further embodiment of the invention is a system for (preferably, arthroscopically) resecting a humeral head and glenoid fossa of a shoulder joint and replacing it with a total shoulder prosthesis, the system comprising:
an implantable humeral component HC which comprises a head part A, affixable or affixed to a base part B;
an implantable glenoid component GC which each which comprises an articular glenoid part C, affixable or affixed to a glenoid base plate part D;
optionally but preferably at least one of:
an osteotomy guide OG;
a guide instrument GI;
a compression instrument CI;
a locator instrument LI,
one or more reciprocating mini saw blades; and
one or more boring reamers.

In preferred embodiments, the foregoing system necessarily comprises at least one of: an osteotomy guide OG; a guide instrument GI; a compression instrument CI; a locator instrument LI, but in certain preferred embodiments comprises at least two of, more preferably at least all three, and especially preferably all four of the foregoing.

The invention claimed is:

1. A system of parts configured for use in resecting a humeral head and glenoid fossa of shoulder joint and replacing it with a total shoulder prosthesis, the system comprising:
an implantable humeral component which comprises a head part affixable to or affixed to a base part, a central peg having a base, an axial threaded recess extending inwardly from the base, and an alignment recess extending inwardly from the base, which alignment recess has a complementary geometry to the geometry of an engaging tip of an instrument, which instrument is insertable through a part of the humerus to allow engagement of the alignment recess with the engaging tip of the inserted instrument;
an implantable glenoid component which comprises an articular glenoid part affixable or affixed to a glenoid base plate part;
optionally, at least one of:
an osteotomy guide;
a guide instrument;
a compression instrument;
a locator instrument;
one or more reciprocating mini saw blades; and
one or more boring reamers.

2. The system of claim 1, wherein the humeral component further comprises a head having an articular bearing surface having a flat back surface and a central recess configured to receive and retain within it an insert portion of a fixation portion.

3. The system of claim 2, wherein the base part of the humeral component comprises a fixation portion having the insert portion configured to be received within the central recess, and at least one transverse hole within the central peg for receiving a locking fixation screw.

4. The system of claim 3, wherein the base part of the humeral component includes a circular disc which extends radially outwardly from the base part and is situated between the insert part and central peg.

5. The system of claim 1, wherein the base plate of the glenoidal component includes a generally flat glenoid base plate and a cavity configured to receive and retain within it the base of an articular glenoid part.

6. The system of claim 1 which comprises a guide instrument which includes a center locating part having squeezable claws, an attachment channel and a detachable outrigger.

7. The system of claim 1 which comprises an osteotomy guide having a centering device at a distal end of an arm which has lateral expandable brackets and proximal end of arm includes a bracket part to which is affixed a cutting guide having a lateral slot angled between about 30°-70° of inclination with respect to a center line of the arm.

8. The system of claim 1 which comprises a compression instrument having a slideable shaft having threads at opposite ends thereof, a sleeve body having a distal end, a shoulder at a proximal end, and a rotation knob, wherein the shaft is insertable within the sleeve body, threads at one end thereof are configured to engage with the axial threaded recess of the base part of a humeral component implanted within a humerus, and threads at the opposite end thereof are configured to engage the rotation knob, and wherein rotation of the knob urges the shoulder against a part of the humerus, and causes the base part to move into a central recess present in the humerus.

9. The system of claim 1 which comprises a locator instrument having a hollow locating sleeve having a proximal part having at its proximal end thereof an engaging tip, which has a complementary geography to that of the alignment recess of the base part, and a distal part thereof conjoined with the proximal part, and a locator outrigger removably affixed to a part of the distal part, the locator outrigger having a locator hole which overlays the position of a hole of a base part implanted within a humerus when locator outrigger is mounted relative to a hole reference position present on the locating sleeve.

10. An implantable humeral component which comprises a head part affixable to or affixed to a base part, a central peg having a base, an axial threaded recess extending inwardly from the base, and an alignment recess extending inwardly from the base, which alignment recess has a complementary geometry to an engaging tip of an instrument, which instrument is insertable through a part of the humerus to allow engagement of the alignment recess with the engaging tip of the inserted instrument.

11. The implantable humeral component of claim 10, which further comprises a head having an articular bearing surface having a flat back surface and a central recess configured to receive and retain within it an insert portion of a fixation portion.

12. The implantable humeral component of claim 11, which further comprises at least one transverse hole within the central peg for receiving a locking fixation screw.

13. A total shoulder prosthesis comprising:
an implantable humeral component which comprises a head part affixable to or affixed to a base part, a central peg having a base, an axial threaded recess extending inwardly from the base, and an alignment recess extending inwardly from the base, which alignment recess has a complementary geometry to the geometry of an engaging tip of an instrument, which instrument is insertable through a part of the humerus to allow engagement of the alignment recess with the engaging tip of the inserted instrument;
an implantable glenoid component which comprises an articular glenoid part affixable or affixed to a glenoid base plate part.

14. The total shoulder prosthesis of claim 13, wherein the humeral component further comprises a head having an articular bearing surface having a flat back surface and a central recess configured to receive and retain within it an insert portion of a fixation portion.

15. The total shoulder prosthesis of claim 13, wherein the base part of the humeral component comprises a fixation portion having the insert portion configured to be received within the central recess, and at least one transverse hole within the central peg for receiving a locking fixation screw.

16. The total shoulder prosthesis of claim 13, wherein the base part of the humeral component includes a circular disc which extends radially outwardly from the base part and is situated between the insert part and central peg.

* * * * *